United States Patent
Zhu et al.

(10) Patent No.: US 10,939,892 B2
(45) Date of Patent: Mar. 9, 2021

(54) COLLIMATOR, RADIATION EMITTING ASSEMBLY AND INSPECTION APPARATUS

(71) Applicants: Tsinghua University, Beijing (CN); Nuctech Company Limited, Beijing (CN)

(72) Inventors: Guoping Zhu, Beijing (CN); Qitian Miao, Beijing (CN); Junli Li, Beijing (CN); Xiaoli Zhang, Beijing (CN)

(73) Assignees: Nuctech Company Limited, Beijing (CN); Tsinghua University, Beijing (CN)

(*) Notice: Subject to any disclaimer, the term of this patent is extended or adjusted under 35 U.S.C. 154(b) by 65 days.

(21) Appl. No.: 15/827,708

(22) Filed: Nov. 30, 2017

(65) Prior Publication Data

US 2018/0160997 A1    Jun. 14, 2018

(30) Foreign Application Priority Data

Dec. 8, 2016 (CN) .......................... 201611128121.X

(51) Int. Cl.
*A61B 6/03* (2006.01)
*G21K 1/02* (2006.01)
(Continued)

(52) U.S. Cl.
CPC .............. *A61B 6/583* (2013.01); *A61B 6/03* (2013.01); *G01N 23/046* (2013.01); *G02B 27/30* (2013.01);
(Continued)

(58) Field of Classification Search
CPC ........ A61B 6/583; A61B 6/03; G01N 23/046; G02B 27/30; G21K 1/02; G21K 1/025; G21K 1/12
See application file for complete search history.

(56) References Cited

U.S. PATENT DOCUMENTS

| | | | | |
|---|---|---|---|---|
| 4,198,570 A | * | 4/1980 | McHugh | ............... A61N 5/10 378/158 |
| 2004/0184577 A1 | * | 9/2004 | Carlsson | ............ A61N 5/1084 378/65 |

(Continued)

FOREIGN PATENT DOCUMENTS

| | | | | |
|---|---|---|---|---|
| CN | 101266844 A | | 9/2008 | |
| CN | 201126720 Y | * | 10/2008 | ............. G21C 17/04 |

(Continued)

OTHER PUBLICATIONS

Hong—CN 2011-26720 Y—English Translation obtained from Google Patents on Mar. 29, 2019 (Year: 2019).*

(Continued)

*Primary Examiner* — David P Porta
*Assistant Examiner* — Jeremy S Valentiner
(74) *Attorney, Agent, or Firm* — Schwegman Lundberg & Woessner, P.A.

(57) ABSTRACT

There are disclosed a collimator, a radiation emitting assembly and an inspection apparatus. The collimator is configured to collimate radiation from a radiation emitter. One of the collimator and the radiation emitter is provided with a protrusion portion and the other is provided with a recess portion such that the protrusion portion is capable of being placed within the recess portion and the radiation emitter and the collimator are allowed to be arranged close to and connected with each other, and that the radiation passes through passages in the protrusion portion and the recess portion from the radiation emitter to the collimator.

17 Claims, 1 Drawing Sheet

(51) Int. Cl.
  *G02B 27/30* (2006.01)
  *A61B 6/00* (2006.01)
  *G01N 23/046* (2018.01)
  *G21K 1/12* (2006.01)

(52) U.S. Cl.
  CPC ............... *G21K 1/02* (2013.01); *G21K 1/025* (2013.01); *G21K 1/12* (2013.01)

(56) References Cited

U.S. PATENT DOCUMENTS

| | | | | |
|---|---|---|---|---|
| 2005/0190890 | A1* | 9/2005 | Schmitt | A61B 6/08 378/206 |
| 2012/0043471 | A1* | 2/2012 | Harpring | G01T 7/00 250/394 |
| 2015/0187535 | A1* | 7/2015 | Tang | H01J 35/14 378/42 |
| 2015/0377804 | A1* | 12/2015 | Arsenault | G01N 23/20066 250/393 |
| 2017/0032864 | A1* | 2/2017 | Yoshimizu | G21K 1/02 |
| 2018/0277272 | A1* | 9/2018 | Park | G21F 3/00 |

FOREIGN PATENT DOCUMENTS

| | | | |
|---|---|---|---|
| CN | 201126720 | Y | 10/2008 |
| CN | 103990232 | A | 8/2014 |
| CN | 104345335 | A | 2/2015 |
| CN | 104813436 | A | 7/2015 |
| CN | 105702312 | A | 6/2016 |
| CN | 105788690 | A | 7/2016 |
| CN | 206236434 | U | 6/2017 |
| JP | 2003114203 | A * | 4/2003 ............ G01N 23/04 |
| JP | 2003294658 | A * | 10/2003 |
| JP | 2013109902 | A * | 6/2013 ............ G01N 23/04 |

OTHER PUBLICATIONS

Izumi et al.—JP 2003-114203 A—English Translation obtaine from AIPN JPO translation services on Mar. 29, 2019 (Year: 2019).*
Ogura et al.—JP 2013-109902 A Google Patent English Translation obtained Jun. 17, 2020 (Year: 2020).*
Yamaguchi et al.—JP 2003-294658 A Google Patents English Translation obtained Jun. 16, 2020 (Year: 2020).*
"Chinese Application No. 201611128121.X Office Action dated Oct. 10, 2017", w/English Translation, (Oct. 10, 2017), 12 pgs.

* cited by examiner

2(a)

2(b)

COLLIMATOR, RADIATION EMITTING ASSEMBLY AND INSPECTION APPARATUS

CROSS-REFERENCE TO RELATED APPLICATION

The present application claims priority to Chinese Patent Application No. 201611128121.X, filed on Dec. 8, 2016, entitled "COLLIMATOR, RADIATION EMITTING ASSEMBLY AND INSPECTION APPARATUS", which is incorporated herein by reference in its entirety.

BACKGROUND

Technical Field

Embodiments of the present disclosure relate to technical field of radiation inspection, and particularly to a collimator, a radiation emitting assembly and an inspection apparatus.

Description of the Related Art

Generally, radiation provided directly by an accelerator or isotope source cannot meet requirement in practice and is needed to be restricted by a collimator according to actual requirement. A design of a collimator directly affects imaging quality and radiation dose level in ambience around the source. Meanwhile, a weight and manufacturing cost of a collimator are also factors related to the entire performance of the system. A conventional collimator is designed in a principle where radiation is firstly released and subsequently collimated, that is, a great deal of radiation is firstly emitted and then collimated and shielded. As the radiation is often divergent, such design principle directly results in an overlarge volume of the collimator and increased difficulty of shielding of the radiation scattered from the collimator. The conventional collimator generally includes two rectangle collimating blocks in a larger volume and is provided with additional wings at a collimator inlet and outlet to shield the scattering radiation, and thus has an overlarge volume, a large weight and a high manufacturing cost.

SUMMARY

According to an aspect of the present disclosure, there is provided a collimator, which is configured to be connected with a radiation emitter configured to emit radiation, one of the collimator and the radiation emitter is provided with a protrusion portion and the other is provided with a recess portion such that the protrusion portion is capable of being placed within the recess portion and the radiation emitter and the collimator can be arranged close to each other, and the radiation passes through passages in the protrusion portion and the recess portion from the radiation emitter to the collimator.

According to an aspect of the present disclosure, there is provided a radiation emitting assembly including the collimator as described above.

According to an aspect of the present disclosure, there is provided an inspection apparatus including the radiation emitting assembly as described above and detectors, the detectors are arranged in a shape corresponding to the cross section of the radiation emitted by the radiation emitting assembly.

DETAILED DESCRIPTION OF THE EMBODIMENTS

Figure 1:
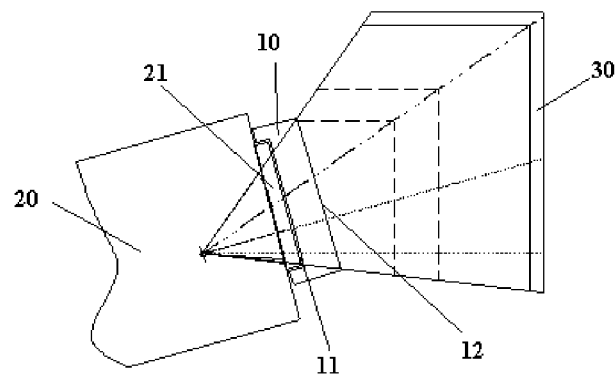
FIG. 1 is a schematic cross sectional view of an inspection apparatus according to an embodiment of the present disclosure.

Embodiments of the present disclosure are exemplarily shown in the drawings and described in detail in the following text although various modification and alternatives are permitted. However, it is appreciated that the attached drawings and the detailed description thereof are not intended to limit the present disclosure to the specific embodiments, instead of, being intended to cover all modifications, equivalent and substitution of the present disclosure made in spirit and scope defined by the attached claims. The drawings are provided for illustration and are not made with a scale.

A plurality of embodiments of the present disclosure will be described with reference to the drawings.

An embodiment of the present disclosure provides a collimator 10 arranged near an outlet of a radiation emitter 20 that emits a radiation. In the embodiment, one of the collimator 10 and the radiation emitter 20 is provided with a protrusion portion 21 and the other is provided with a recess portion 11 such that the protrusion portion 21 can be placed within the recess portion 11 and the radiation emitter 20 and the collimator 10 can be close to and connected with each other, and the radiation passes through a passage of the protrusion portion and the recess portion from the radiation emitter 20 to the collimator 10.

FIG. 1 illustrates an embodiment of the present disclosure, in which the radiation emitter 20 has a protrusion portion 21 while the collimator 10 has a recess portion 11. In an existing apparatus, a radiation emitter and a collimator are hard to be close to each other in practice due to their large volumes and irregular shapes, and thus a shield piece or shield article is needed to be disposed between them to shield radiation, avoiding the radiation from leaking at connection or coupling between the radiation emitter and the collimator and damaging person near them, which results the entire apparatus or system having a very large volume. In order for mating the radiation emitter with the collimator, a manufacturing process of the entire apparatus becomes complex and its cost increases.

In the embodiment of the present disclosure, the protrusion portion 21 of the radiation emitter 20 may be inserted into the recess portion 11 of the collimator 10. With this configuration, even though other parts of the radiation emitter 20 were not close to the collimator 10 due to their irregular shapes or other factors, a part, i.e., the protrusion portion 21, of the radiation emitter 20 may be inserted into the recess portion 11 of the collimator 10 to achieve connection between the radiation emitter 20 and the collimator 10, such that the radiation passes through a passage in the protrusion portion 21 and the recess portion 11 from the radiation emitter to the collimator and thus will not be leaked out to external, or just a small quantity of radiation scatters or leaks out to external. With this configuration, shield of radiation may be achieved by means of simple connection or combination or even by modifying existing apparatuses, and thus the manufacturing cost of the entire apparatus is reduced. In an embodiment, a gap may exist between the radiation emitter 20 and the collimator 10, that is, it is not necessary to closely contact the radiation emitter 20 with the collimator 10. Due to engagement between the protrusion portion 21 and the recess portion 11 provided by the embodiment, radiation will not be leaked even though the protrusion portion 21 and the recess portion 11 did not closely contact with each other, which thus ensures safety, enables a great freedom during design and manufacture of the apparatus and is important during practical production. FIG. 1 is a schematic view of the inspection apparatus, in which sizes of components do not represent actual sizes of them and may be configured according to actual requirements.

In another embodiment of the present disclosure, the collimator is provided with a protrusion portion and the radiation emitter is provided with a recess portion.

In embodiments of the present disclosure, sizes of the protrusion portion and the recess portion are not specifically defined and may be configured according to requirements, such as intensity of the radiation, sizes of the radiation emitter and the collimator.

Figure 2:
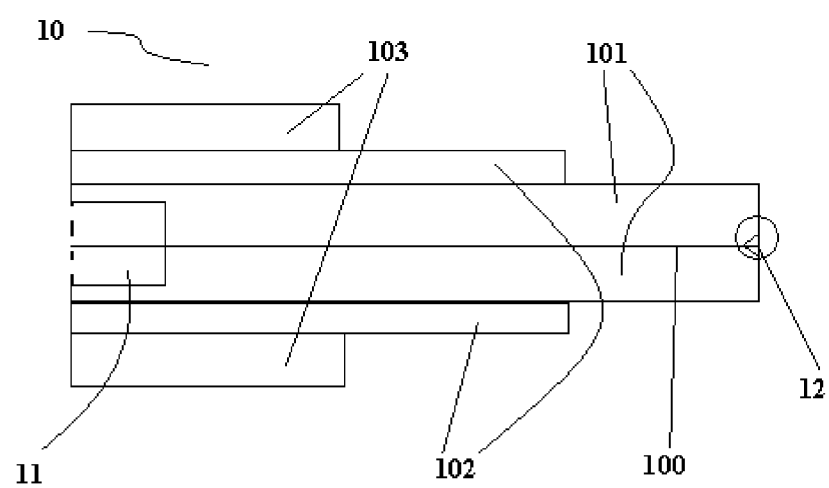
FIG. 2(a) is a schematic cross sectional view of a collimator according to an embodiment of the present disclosure and FIG. 2(b) is an enlarged view of a local part, in the circle in FIG. 2(a), of a primary collimator component.
Figure 2:

According to an embodiment of the present disclosure, the collimator 10 includes at least two primary collimator components 101. The at least two primary collimator components 101 are configured to provide a slit or a passage 100 therebetween to collimate radiation and, a collimator outlet is provided at one end of the slit or passage and configured to emit the radiation. In the embodiment, one of the protrusion portion 21 and the recess portion 11 is disposed in or on the at least two primary collimator components 101. In another embodiment, the protrusion portion or the recess portion may be configured on other components of the collimator 10 and continuous with the collimator components. In the embodiment as shown in FIG. 2, two primary collimator components 10 are provided.

According to an embodiment of the present disclosure, the at least two primary collimator components 101 are configured such that a cross section of the radiation emitted from the collimator outlet corresponds to an arrangement shape of the detectors 30. In another embodiment, the at least two primary collimator components 101 are configured such that a cross section of the radiation emitted from the collimator outlet is consistent with (e.g., identical to) an arrangement shape of the detectors 30. For example, the cross section of the radiation emitted from the collimator 10 and the arrangement shape of detector 30 are each in a form of inverted "L". In other embodiments, the cross section of the radiation emitted from the collimator 10 and the arrangement shape of detector 30 are configured in a form of "I", "[", "]", "T", "Π", "∩" or others. In order to obtain desired radiation profile, more two primary collimator components 101 may be used.

According to an embodiment of the present disclosure, the at least two primary collimator components 101 are configured such that an area of a cross section, which is perpendicular to a radiation emitting direction, of an opening in the collimator near the collimator outlet gradually increases in the radiation emitting direction. As shown in FIG. 2, the at least two primary collimator components 101 are provided with recesses near the collimator outlet 12. For example, portions of the at least two primary collimator components 101 near the collimator outlet each have a slope (which is illustrated in an enlarged view in FIG. 2) adjacent to the radiation emitting side such that the area of the cross section of the opening of the collimator 10 at the collimator outlet 12 is gradually increasing in the radiation emitting direction. In an embodiment, a plurality of primary collimator components 101 constitute the collimator 10, and each have a slope, near the collimator outlet 12, on a side thereof which defines the radiation slit or passage of the collimator 10, such that an area of the cross section of the opening is gradually increasing in the radiation emitting direction. In another embodiment, the collimator 10 has an inwardly recessed taper outlet portion near the collimator outlet 12. With the configuration of the collimator outlet 12, scattering of the radiation is eliminated.

According to an embodiment of the present disclosure, the at least two primary collimator components 101 are respectively provided with at least a pair of additional shield pieces 102, 103 on an outer side thereof facing away from the passing radiation. In another embodiments, the at least two primary collimator components 101 are respectively provided with at least two pairs of additional shield pieces 102, 103 on the outer side thereof. The at least two pairs of additional shield pieces 102, 103 are arranged to stack together and overlap with each other at a position, adjacent to the radiation emitter 20, of the outer side of the at least two primary collimators components 101 and the stacking area between the additional shield pieces 102, 103 is gradually reduced in the radiation emitting direction, such that the area of the cross section of the collimator is gradually reduced in the radiation emitting direction while ensuring shielding effect to the radiation.

In an embodiment, the at least two pairs of additional shield pieces 102, 103 include a first pair of additional shield pieces 102 and a second pair of additional shield pieces 103. The first pair of additional shield pieces 102 and the second pair of additional shield pieces 103 are both close to the radiation emitter 20, the second pair of additional shield pieces 103 are arranged on the first pair of additional shield pieces 102 and a length of the second pair of additional shield pieces 103 is less than a length of the first pair of additional shield pieces 102. Thicknesses of the first pair of additional shield pieces 102 and the second pair of additional shield pieces 103 may be the same as or may be different from each other, and may be configured according to actual requirements.

In the illustrated embodiment, a passage 100 for passing the radiation is formed between the two primary collimator components 101. A notch or recess as shown in FIG. 2(a) is formed in the two primary collimator components 101 near the outlet 12 (that is the collimator outlet 12). That is, a slope is formed at a side, facing the passing radiation, of each of the primary collimator components 101 and thus the two primary collimator components 101 define an opening or passage that is gradually increasing in the radiation emitting direction. That is, the area of the cross section of the opening is gradually increasing in the radiation emitting direction. In an embodiment, when a cross section of the passage 100 for passing the radiation is circular or square, the cross section at the opening may be formed in a shape of taper. The additional shield pieces 102, 103 are provided on an outer side, i.e., a side facing away from the radiation, of each of the two primary collimator components 101. The additional shield pieces 102, 103 are disposed as shown in FIG. 2(a), that is, the first additional shield pieces 102 are arranged to closely abut against the primary collimator component 101 and the second additional shield pieces 103 are arranged on the first additional shield pieces 102. The length of the second additional shield pieces 103 is less than a length of the first additional shield pieces 102. The first and second additional shield pieces are both arranged to close to the radiation emitter 20. As shown in FIG. 2(a), the first additional shield pieces 102 and the second additional shield pieces 103 are arranged such that a volume of the collimator 10 gradually reduces in a direction from the radiation emitter 20 towards the collimator outlet, or, in other words, the cross section of the collimator 10 is gradually reduced in the direction from the radiation emitter towards the collimator outlet. With this arrangement, the volume and weight of the collimator 10 may be reduced while a shielding effect on the radiation may be ensured.

According to an embodiment of the present disclosure, the primary collimator components 101 are made of lead or tungsten. The additional shield pieces 102, 103 are made of lead or tungsten.

According to an aspect of the present disclosure, there is provided a radiation emitting assembly comprising the collimator 10 as described above.

According to an aspect of the present disclosure, there is provided an inspection apparatus including the radiation emitting assembly as described above and detector, wherein the detectors are arranged to have a shape corresponding to the cross section of the radiation emitted by the radiation emitting assembly. The cross section of the radiation is in a shape of inverted "L" and the array of the detectors is arranged in a shape of inverted "L" such that the radiation emitted is received by the corresponding array of the detectors.

Although embodiments of the general concept of the present disclosure have been illustrated and described, it is appreciated by those skilled in the art that the embodiments may be modified without departing from the principle and spirits of the general concept. The protective scope of the present disclosure is defined by the claims and their equivalents.

The invention claimed is:

1. A collimator, configured to collimate radiation from a radiation emitter, the collimator comprising: a protrusion portion such that the protrusion portion is capable of being placed within a recess portion of the radiation emitter, wherein the collimator is allowed to be arranged close to and connected with the radiation emitter, and wherein the radiation passes through passages in the protrusion portion and the recess portion from the radiation emitter to the collimator, wherein the collimator includes at least two primary collimator components configured to provide a slit therebetween to collimate the radiation and defining a collimator outlet configured to emit the radiation; and the at least two primary collimator components are provided with the protrusion portion, and wherein the at least two primary collimator components are respectively provided with at least a pair of additional shield pieces on an outer side thereof opposite to an inner side facing the radiation.

2. The collimator according to claim 1, wherein the at least two primary collimator components are configured such that a cross section of the radiation emitted from the collimator outlet corresponds to an arrangement shape of detectors configured to receive the radiation such that the cross section of the radiation emitted from the collimator outlet is identical to the arrangement shape of the detectors.

3. The collimator according to claim 1, wherein the at least two primary collimator components are configured such that an area of a cross section of an opening in the collimator near the collimator outlet gradually increases in a radiation emitting direction such that the collimator has an inwardly recessed taper outlet portion at the collimator outlet.

4. The collimator according to claim 3, wherein the at least two primary collimator components are configured to respectively have a slope located at a side facing the radiation and near the collimator outlet such that the area of the cross section of the opening in the collimator near the collimator outlet gradually increases in the radiation emitting direction.

5. The collimator according to claim 1, wherein the at least two primary collimator components are respectively provided with at least two pairs of additional shield pieces on the outer side thereof.

6. The collimator according to claim 5, wherein at least two pairs of additional shield pieces are arranged to stack together and overlap with each other at a position, adjacent to the radiation emitter, on the outer side of the at least two primary collimator components and a stacking area between the pairs of additional shield pieces gradually reduces in the radiation emitting direction, such that the area of a cross section of the collimator is reduced gradually in the radiation emitting direction.

7. The collimator according to claim 6, wherein the at least two pairs of additional shield pieces include a first pair of additional shield pieces and a second pair of additional shield pieces, the first pair of additional shield pieces and the second pair of additional shield pieces are both arranged adjacent to the radiation emitter, the second pair of additional shield pieces are arranged on the first pair of additional shield pieces and a length of the second pair of shield pieces is less than a length of the first pair of shield pieces.

8. The collimator according to claim 1, wherein the primary collimator components and the additional shield pieces are made of lead or tungsten.

9. A radiation emitting assembly comprising the collimator according to claim 1.

10. An inspection apparatus comprising the radiation emitting assembly according to claim 9 and detectors, wherein the detectors are arranged in a shape corresponding to the cross section of the radiation emitted by the radiation emitting assembly.

11. A collimator, configured to collimate radiation from a radiation emitter, the collimator comprising: a recess portion configured such that a protrusion portion of the radiation emitter is capable of being placed within the recess portion, wherein the collimator is allowed to be arranged close to and connected with the part of the radiation emitter other than the protrusion portion with the protrusion portion being received within the recess portion of the collimator, and the radiation passes through passages in the protrusion portion and the recess portion from the radiation emitter to the collimator, wherein the collimator includes at least two primary collimator components configured to provide a slit therebetween to collimate the radiation and defining a collimator outlet configured to emit the radiation, wherein the at least two primary collimator components are provided with the recess portion, and wherein the at least two primary collimator components are respectively provided with at least a pair of additional shield pieces on an outer side thereof opposite to an inner side facing the radiation.

12. The collimator according to claim 11, wherein the at least two primary collimator components are configured such that a cross section of the radiation emitted from the collimator outlet corresponds to an arrangement shape of detectors configured to receive the radiation such that the cross section of the radiation emitted from the collimator outlet is identical to the arrangement shape of the detectors.

13. The collimator according to claim 11, wherein the at least two primary collimator components are configured such that an area of a cross section of an opening in the collimator near the collimator outlet gradually increases in a radiation emitting direction.

14. The collimator according to claim 13, wherein the at least two primary collimator components are configured to respectively have a slope located at a side facing the radiation and near the collimator outlet such that the area of the cross section of the opening in the collimator near the collimator outlet gradually increases in the radiation emitting direction.

15. The collimator according to claim 11, wherein the at least two primary collimator components are respectively provided with at least two pairs of additional shield pieces on the outer side thereof.

16. The collimator according to claim 15, wherein at least two pairs of additional shield pieces are arranged to stack together and overlap with each other at a position, adjacent to the radiation emitter, on the outer side of the at least two primary collimator components and a stacking area between the pairs of additional shield pieces gradually reduces in the radiation emitting direction, such that the area of a cross section of the collimator is reduced gradually in the radiation emitting direction.

17. The collimator according to claim 16, wherein the at least two pairs of additional shield pieces include a first pair of additional shield pieces and a second pair of additional shield pieces, the first pair of additional shield pieces and the second pair of additional shield pieces are both arranged adjacent to the radiation emitter, the second pair of additional shield pieces are arranged on the first pair of additional shield pieces and a length of the second pair of shield pieces is less than a length of the first pair of shield pieces.

* * * * *